US010390757B2

(12) United States Patent
Villard et al.

(10) Patent No.: US 10,390,757 B2
(45) Date of Patent: Aug. 27, 2019

(54) SYSTEM AND METHOD TO MONITOR A PHYSIOLOGICAL PARAMETER OF AN INDIVIDUAL

(71) Applicant: WITHINGS, Issy les Moulineaux (FR)

(72) Inventors: Joffrey Villard, Paris (FR); Cédric Hutchings, Issy les Moulineaux (FR)

(73) Assignee: WITHINGS, Issy les Moulineaux (FR)

( * ) Notice: Subject to any disclaimer, the term of this patent is extended or adjusted under 35 U.S.C. 154(b) by 458 days.

(21) Appl. No.: 14/623,253

(22) Filed: Feb. 16, 2015

(65) Prior Publication Data

US 2016/0235356 A1  Aug. 18, 2016

(51) Int. Cl.
*A61B 5/00* (2006.01)
*A61B 5/11* (2006.01)
*A61B 5/0205* (2006.01)
*G09B 19/00* (2006.01)
*G01G 19/414* (2006.01)
*G01G 19/44* (2006.01)
*G01G 19/50* (2006.01)

(52) U.S. Cl.
CPC .............. *A61B 5/486* (2013.01); *A61B 5/00* (2013.01); *A61B 5/0205* (2013.01); *A61B 5/1102* (2013.01); *A61B 5/4815* (2013.01); *A61B 5/4866* (2013.01); *A61B 5/7282* (2013.01); *G09B 19/00* (2013.01); *A61B 2560/0242* (2013.01); *A61B 2560/0475* (2013.01); *G01G 19/4146* (2013.01); *G01G 19/44* (2013.01); *G01G 19/50* (2013.01)

(58) Field of Classification Search
USPC ........................................................ 434/236
See application file for complete search history.

(56) References Cited

FOREIGN PATENT DOCUMENTS

EP      2685895 A1      1/2014
WO   WO 2007/098577 A1   9/2007
WO   WO 2014/013208 A1   1/2014

*Primary Examiner* — Kesha Frisby
(74) *Attorney, Agent, or Firm* — Miller, Matthias & Hull LLP

(57) ABSTRACT

A method to monitor a data of interest of an individual (U) and give advice to said individual, said method comprising: a—collect said data of interest and a plurality of life parameters, b—monitor the evolution over time of said data of interest, c—detect an unexpected/inadvertent deviation in the evolution of data of interest, forming a break event, occurred at a first instant (T1), d—store the previously collected values of the plurality of life parameters over a first time window preceding said break event, to form a reference values collection of life parameters, attached to said individual and to the break event, and later: e—collect over time, the values of the plurality of life parameters, f—compare said lately collected values of life parameters to the reference values collection of life parameters stored, and if they are similar, give a notice to the user, whereby the user can be warned of a possible imminent deviation related to the data of interest.

14 Claims, 3 Drawing Sheets

SYSTEM AND METHOD TO MONITOR A PHYSIOLOGICAL PARAMETER OF AN INDIVIDUAL

FIELD OF THE DISCLOSURE

The present invention relates to systems and methods of monitoring physiological parameters of an individual.

BACKGROUND OF THE DISCLOSURE

More precisely, the present invention relates to a monitoring system and method, which allows to give advice to the individual (the 'user'), and give personalized coaching to the individual about his/her health.

It is known from EP2685895 a monitoring system to monitor blood glucose level with individualized advice about what action or medicine to take. However, this kind of medical device is intrusive, requires knowledge from the user and does not take into account history of previous behaviour of the patient.

Therefore, there is a need to propose a user-friendly, simple-to-use monitoring system which can you be used beyond medical field by any individual user.

SUMMARY OF THE DISCLOSURE

To this aim, according to the invention, there is provided a method to monitor at least one physiological parameter of interest of an individual and give advice to said individual about said at least one physiological parameter, said method comprising a first set of steps:
a—collect over time, on the one hand, said at least one physiological parameter of interest of the individual and on the other hand a plurality of life parameters,
b—calculate a data of interest from collected samples of the physiological parameter, and monitor the evolution over time of said data of interest,
c—detect an unexpected/inadvertent deviation in the evolution over time of said data of interest, said unexpected/inadvertent deviation forming a break event, occurred at a first instant,
d—store, in remnant memory, the previously collected values of the plurality of life parameters over a first time window preceding said break event, to form a reference values collection of life parameters, attached to said individual and to the break event, said method comprising a later, second set of steps:
e—collect over time, the values of said plurality of the same life parameters,
f—compare said lately collected values of life parameters to the reference values collection of life parameters stored in remnant memory, and if the difference is less than a predefined threshold, give a notice to the individual user.

Whereby the individual user can be warned of a possible imminent deviation related to the data of interest and/or physiological parameter of interest.

The life parameters can be chosen among a list comprising:
geolocation of the individual user,
time in day, moment in week, moment in month, season moment in year,
number of messages exchanged over social network(s),
type of current activity (work, holiday, travelling, sports, visiting friends, visiting family),
level of physical activity, number of steps done per day,
average food intake per meal/day/week,
average alcohol intake per meal/day/week,
tobacco smoking per day/week
drug/medicine consumption per day/week
time spent watching TV (or videos on computer)
environmental parameters around the user (temperature, air quality, pollutants, sound/noise levels)
weight, weight variation,
blood pressure, heart rate variability,
Whereby a large variety of life parameters can be taken into account to detect the conditions favoring a deviation of a physiological parameter.

The physiological parameter of interest can be the weight of the individual, and the data of interest is the weight itself or the weight variation (in particular compared to previous known weight). Whereby the weight of the user can be of particular attention, and an unexpected deviation can be associated with a sequence of life parameters, and the occurrence of a similar sequence of life parameters can cause a notice to be given to the user.

The data of interest can be a sleep quality index and the physiological parameters are ballistographic movements of the user, body temperature, in relation with life parameters like ambient temperature, ambient noise, air quality. Whereby a personalized coaching can thus be provided to the user about his/her sleep quality conditions.

The data of interest can be the collected physiological parameter itself or a derivative of said physiological parameter. This is a simple computation to give the data of interest from the physiological parameter.

Each of the plurality of the life parameters can be sampled/collected and stored momentarily in a rolling window (TR) having a time depth no less than the first time window DT1. This is a simple, straightforward process of data collection At step c—, the detection of an unexpected/inadvertent deviation in the evolution over time of said data of interest can be performed with reference to a predefined interval (81-82) of expected values. This is a simple computation.

At step c—, the detection of an unexpected/inadvertent deviation in the evolution over time of said data of interest can be performed using a CUSUM control chart. This is a reliable and relevant computation to detect parameter deviation.

At step c—, the detection of an unexpected/inadvertent deviation in the evolution over time of said data of interest is performed with reference to a reference curve (C) giving a predefined expected evolution of the data related to the physiological parameter of interest as a function of time or at least one life parameter. This is a refined reference and provides an improved reliable detection, avoids false user notification or false warnings.

The method can result, upon iteration, in the storing in a database of a plurality of break event records, each record comprising the physiological parameter of interest, the time/date of detection of the break event, and the reference values collection of life parameters attached to this break event. Therefore, such a personalized history allows to provide personalized coaching to a user.

The notice to the individual user can be a message including the physiological parameter at concern and the time and circumstances that prevailed when the break event was recorded. Whereby the user can be reminded of the latest occurrence(s) together with the circumstances.

The present disclosure is also directed to a system in which the above method can be carried out.

BRIEF DESCRIPTION OF THE DRAWINGS

Other characteristics and advantages of the invention will readily appear from the following description of two of its embodiments, provided as a non-limitative examples, and of the accompanying drawings.

DETAILED DESCRIPTION OF THE DISCLOSURE

Figure 1:
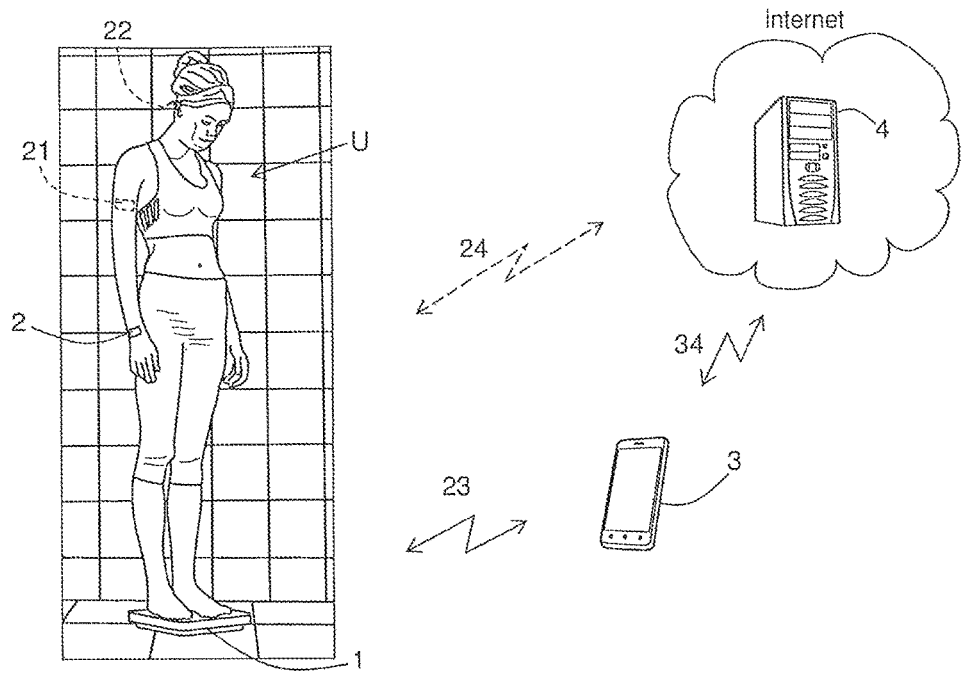
FIG. 1 shows an example of a system in which the invention can be carried out.

FIG. 1 shows a user U (also called "individual" in the following) standing on a weighing scale 1 during an operation of weighing. The weighing scale 1 is an electronic weighing scale as known per se, for example from WO2014/013208.

The user also wears an activity monitoring device 2, worn at the wrist in the shown example. However, such an activity monitoring device 2 can be worn elsewhere, close to the body of the user. Such an activity monitoring is configured to sense accelerations, and therefore can assess the type of activity undertaken by the user, the number of steps done by the user, the caloric burn induced by the current activity, the distance travelled, the positive altitude travelled, etc. Further, the activity monitoring device 2 can optionally measure by photo-plethysmography the heart rate, the blood pressure, the heart rate variability, etc.

In some embodiments, the user might also wear additional sensing apparatus like an electronic miniature earset/earplug 22, of the type known from WO2007098577, or like a blood pressure sensing apparatus 21, as also known per se. Also, the activity monitoring device 2 can be a finger ring or a neck ring, or an ankle ring (not shown).

Other sensing apparatuses are not excluded, including some which are not worn by the user but that come into contact with the user under particular circumstance like when sleeping, and including some of them measuring parameters not directly linked to the user, like the air quality, the temperature, the geolocation, etc., as they will be illustrated notably with the second embodiment.

Further, each of the weighing scale 1, the activity monitoring device 2 and additional sensing apparatuses 21,22 has wireless communication means and is therefore able to exchange data wirelessly with other above-mentioned devices, with BlueTooth™ Low Eenergy ('BLE') or the like.

In the present specification, the weighing scale 1, the activity monitoring device 2 and additional sensing apparatuses 21,22 are able to sense at least one physiological parameter are therefore also referred to generically as "physiological parameter sensor".

Further, at least the weighing scale 1, the activity monitoring device 2 but also additional sensing apparatuses 21,22 have short-range or medium-range wireless communication means (BLE, WIFI or the like) to exchange data 23 with a smartphone 3 forming the user's usual portable communication device. Of course, instead of a smartphone 3, it can be a tablet, a phablet, or the like.

Further, the system according to the invention may include one or more internet server 4, which can be connected 34 to the smartphone 3, as known per se, like cellular network, and therefore not detailed here.

It is not excluded to have a direct wireless link 24 between the weighing scale 1 and the internet server 4. In this first embodiment, the weighing scale 1, the activity monitoring device 2, the smartphone 3 and the internet server 4 constitutes a system 10 in which the below disclosed method can be carried out.

Advantageously according to the present invention, at least one physiological parameter is of particular interest. According to a first practical example (illustrated at FIG. 1), we chose the weight of the individual as to be the physiological parameter of interest.

Besides, the relationship between the physiological parameter of interest and other parameters will be of particular attention; in the context of the present invention, said other parameters are called 'life parameters', said 'life parameters' being representative of various circumstances of the life of the individual at concern, and behaviour of said individual.

To give a first idea, the life parameters can be:
geolocation of the individual user,
time in day, moment in week, moment in month, season in year,
number of messages exchanged over social network(s),
type of current activity (work, holiday, travelling, sports, visiting friends, visiting family),
level of physical activity, number of steps done per day,
average food intake per meal/day/week,
average alcohol intake per meal/day/week,
tobacco (cigarette/cigar) smoking per day/week
environmental parameters around the user (temperature, air quality, pollutants, sound/noise levels)
drug/medicine consumption per day/week,
time spent watching TV (or videos on computer)
weight, weight variation,
blood pressure, heart rate variability, etc.

Therefore, what is understood by 'life parameters' is rather wide, includes physiological data, circumstantial data, behavioural data.

The physiological parameter of interest itself may be studied in relation with life parameters, but also a data of interest which is computed from one of several physiological parameters of interest, as will be seen later.

The plurality of 'life parameters' has the reference numeral 7; in the illustrated example at Figures, each individual life parameter (only six shown) has one reference numeral between 71 and 76.

Figure 2:
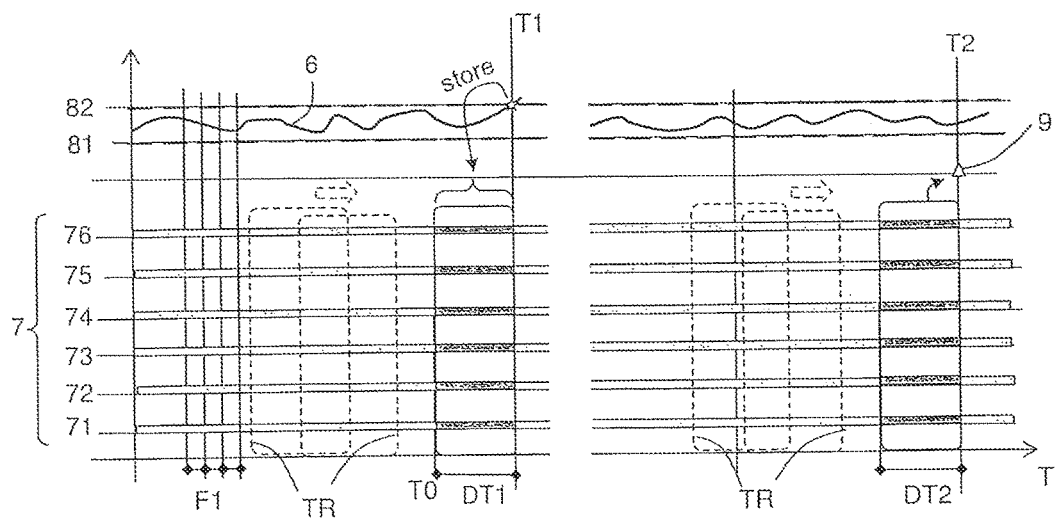
FIG. 2 shows chronographs illustrating the method carried out according to the invention.

Now the method according to the invention is disclosed with reference to FIG. 2. In a first set of steps, the following operations are performed:

Firstly, the system collects over time, on the one hand, at least one physiological parameter of interest 60 of the individual and on the other hand a plurality 7 of life parameters 71-76. This is referred to as step 'a—'.

Secondly, the system computes (calculates) a data of interest 6 from collected samples of the physiological parameter(s), and the system monitors the evolution over time of said data of interest 6.

It should be noted that in most cases, the data of interest 6 is simply equal directly to the physiological parameter 60 itself.

But, in some other cases, the data of interest 6 is different from the physiological parameter itself, it may be the derivative of the physiological parameter, or a more complex calculation.

For example, the data of interest can be the weight variation with reference the previous known latest weighing results.

Figure 5:
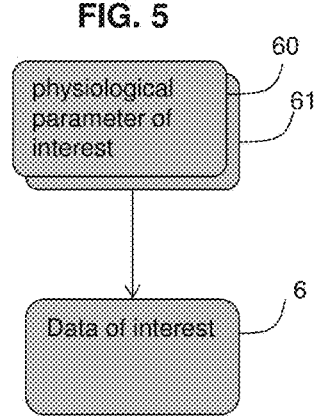
FIG. 5 shows a relationship between physiological parameter(s) of interest and a related data of interest.

Also, the data of interest 6 can be derived either from only one physiological parameter 60, or, as shown in FIG. 5, from two physiological parameters 60,61, or even more than two physiological parameters.

In other words, at step b—of the method, the data of interest 6 is calculated from collected samples of the physiological parameter(s). The evolution over time of said data of interest is then monitored with particular attention.

This monitoring of said data of interest 6 can lead to the detection of an unexpected/inadvertent deviation in the evolution over time of said data of interest with reference to expected values over time. Said unexpected/inadvertent deviation forms what is called a "break event" or a 'inflection event", occurred at a first instant T1. This is referred to as step 'c—'. Said unexpected/inadvertent deviation can be defined in different manners that will be described later.

In case such a break event is indeed detected, the system stores (step 'd—'), in remnant memory, the previously collected values of the plurality of life parameters over a first time window DT1 (T0-T1) preceding said break event, to form a reference values collection of life parameters, attached to said individual and to the break event. A record of the break event comprises the physiological parameter of interest, data of interest, the time/date of detection of the break event, and the reference values collection of life parameters attached to this break event.

Steps a—, b—, c—, and d—form together a first set of steps, called break event detection process.

The detection of the unexpected/inadvertent deviation in the evolution over time of the data of interest can be, as shown at FIG. 2, performed with reference to a predefined interval 81-82 of expected values, i.e. the normal range for the data of interest. If the data of interest 6 becomes lower than a lower limit value or exceeds an upper limit value, then an unexpected/inadvertent deviation is acknowledged, and a break event is declared.

The current time is recorded as the break event timestamp, together with the reference values collection of life parameters attached to this break event.

Further, the method comprises a later, second set of steps, intended to notify the user with an occurrence of similar life parameters of a recorded break event.

Generally speaking, the system permanently monitors th physiological parameters of interest 60 of an individual, and furthermore the system permanently collects over time, the values of each of said plurality of life parameters 7, preferably the same life parameters that was collected to detect one or more break event. This is referred to as step 'e—' of the method.

Further, the system permanently compares said monitored/collected values of life parameters to the reference values collection of life parameters stored in remnant memory. In case the difference is less than a predefined threshold (occurrence of similar life parameters conditions), the system gives a notice 9 to the individual user (step 'f—' of the method).

It is to be noted that the detection and collection of break events is advantageously performed permanently.

In a simple, basic example, the data of interest (here weight of user) is equal to one physiological parameter, and the time scale is rather long, let's say one or two samples per day, and life parameters at particular concern are:

71—level of physical activity, i.e. number of steps done per day,

72—food intake per day,

73—alcohol intake per day,

During a time period DT1, it happens that the user does less physical exercise, takes more food and more alcohol. As a consequence, at instant T1, the weight 6 of the user is found to exceed the maximum expected value 82. The system thus record a break event at T1, and stores at least the sample values of: number of steps done per day 71, food intake per day 72, alcohol intake per day 73, over DT1. This constitutes a break event record in the remnant memory that will be used later.

Later, at time period DT2, similar conditions are collected about number of steps done per day 71, food intake per day 72, alcohol intake per day 73. Therefore, a user notification is issued by the system to warn the user, because since same causes produce same effects, that the user might exceed the maximum weight targeted value if he/she does not change his/her behavior. This can be done irrespective of the current weight, or made dependent on the current weight (stronger warning if the value is closed to maximum expected value 82).

It is to be noted that the second time DT2 can be shorter than the first time period DT1, so as to provide an early warning.

Also, the notification can be triggered by only two life parameters instead of the three (in case for example the alcohol intake is not available).

Another practical example, less straightforward, still related to weight monitoring of the user, is given below. Let's imagine the user is visiting friends for a week, at a particular geolocation, and practice game or watching TV most of the day with these friends. The user does less physical activity, but does not take more food or alcohol; nevertheless, after four days, the weight 6 of the user is found to exceed the maximum value expected. The system thus record a break event at T1, and stores at least the sample values of: number of steps done per day 71, geolocation 74, time spent watching TV/screen 77, over DT1.

Later, the next time the user will be visiting these friends, at time period DT2, similar conditions are collected about number of steps done per day 71, geolocation (assumed as at his friends' home) 74, time spent watching TV/screen. Therefore, a user notification is issued by the system to warn the user, because same causes produce same effects, that the user might exceed the maximum weight targeted value if he/she does not change his/her behavior (better balance of exercise/screen activity).

Instead of a predefined interval of expected values, the inadvertent deviation can be obtained via a CUSUM control chart (CUSUM standing for CUMulative SUM) often used in quality control methods to detect deviations from benchmark values.

Figure 3:
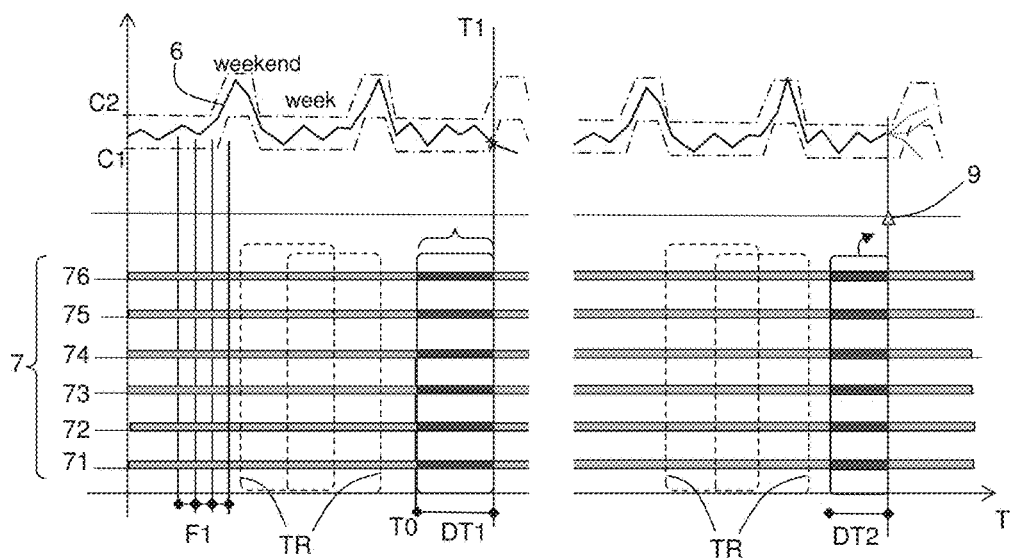
FIG. 3 is analogous to FIG. 2 and shows a variant example.

According to a variant of the first embodiment (FIG. 3), the detection of the unexpected/inadvertent deviation in the evolution over time of the data of interest is performed with reference to a reference range function of time C1-C2 giving a predefined expected evolution of the data related to the physiological parameter of interest as a function of time or at least one life parameter.

This may be the case for the number of steps done per day taken as the data of interest under concern. During the week (Monday to Friday) the level of activity corresponds to walking to worksite and coming back to home, whereas during weekends (Saturday-Sunday) the user practices jogging and/or cycling, which results in a much higher daily level of physical activity.

According to another variant of the first embodiment (FIG. 6), the detection of the unexpected/inadvertent deviation in the evolution over time of the data of interest is performed with reference to a reference curve C with upper limit C2 and lower limit C1 giving a predefined expected evolution of the data related to the physiological parameter of interest as a function of time or at least one life parameter. This will be detailed below with the second embodiment.

The reference curve C can be a data known in advance from some general abacus for example, although reference curve C can also be learnt from past analysis of some parameters relating to the individual of interest over a rather long term. For example, a running average over a week can be used to determine on the long run the habit of the user, and this can constitute a base to build a personalized reference curve C.

For example, a curve of weight versus season can be found by learning as explained before, e.g. over the last three years, such that a weight decrease during summer time and a weight slight increase during winter time can be acknowledge as a normal seasonal variation.

Advantageously, the notice given to the individual user is a message 9 including the physiological parameter at concern and the time and circumstances that prevailed when the break event was recorded. Thereby, the user can be warned of a possible imminent deviation related to the data of interest and/or physiological parameter of interest.

According to a second embodiment, the data of interest is a sleep quality index, which is constructed from ballistographic/movement of the user, body temperature, heart rate.

Figure 7:
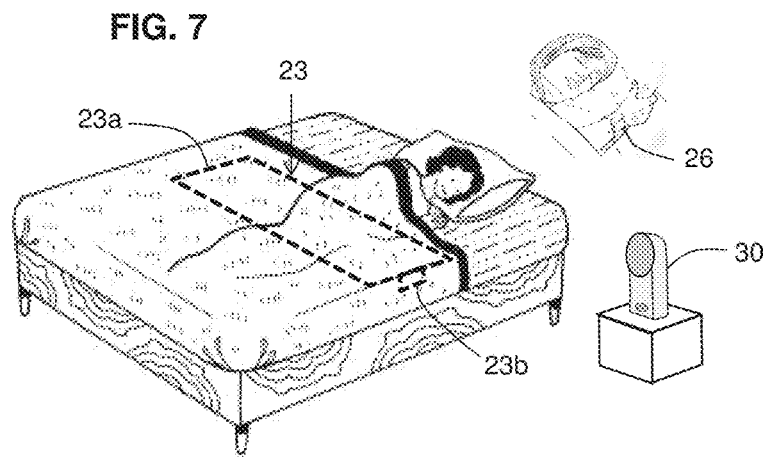
FIG. 7 shows a user in a sleeping configuration.
Figure 8:
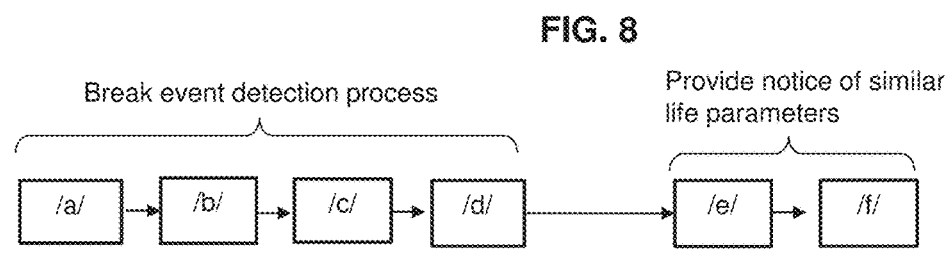
FIG. 8 is a chart illustrating the method.

With reference to FIG. 7, there is provided a bed mat sensor 23, formed for example as a pneumatic inflatable bladder 23a, linked to an electronic unit 23b which transduces pressure information into user movement information and transmit this data to a bedside unit 30.

Additionally, the user might wear a body monitoring device 26 analogous to the activity monitoring device 2 already mentioned above. Body temperature and heart rate or made available through this sensor.

A composite information, known as 'sleep quality index', can be calculated from the collection of all the body movements along the night. More precisely, the bedside unit 30 is able to assess the user's sleep phases (such as light sleep, deep sleep, REM [Rapid Eye Movement also known as sleep 'paradoxical' sleep], etc.) based on the sensory data (movements, heart rate, temperature). The longer each sleep phase, the better the sleep quality is. Therefore it can be computed a 'sleep quality index' which is representative of the length and balance of the different user's sleep phases over the night.

The calculated 'sleep quality index' can be compared, in a simple example to a predefined interval 81-82 of expected values as shown in FIG. 2.

Figure 6:
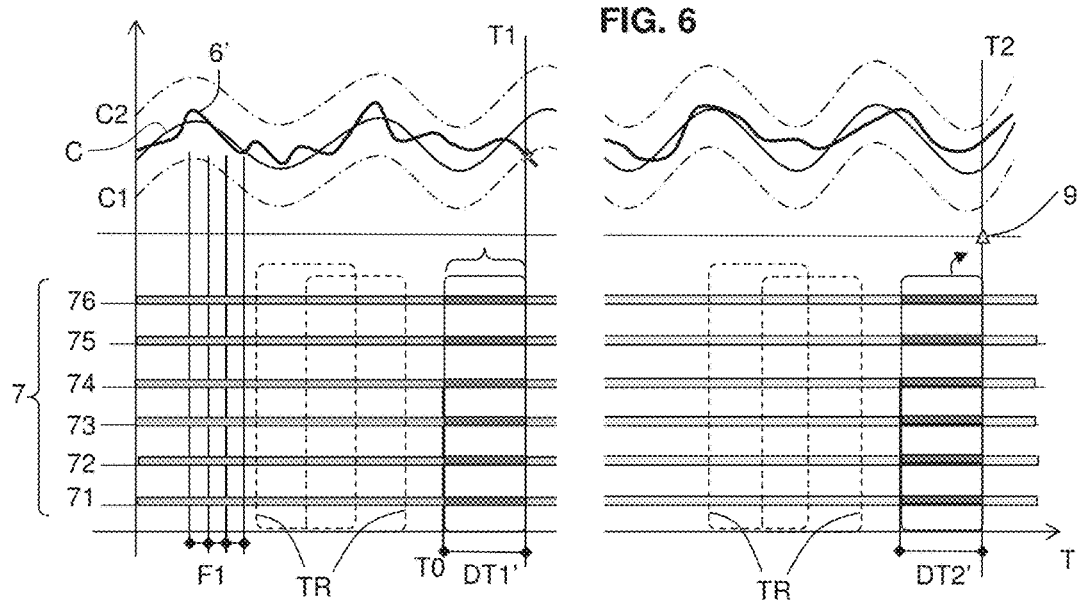
FIG. 6 is analogous to FIG. 2 and shows a variant example.

However, for female users, the calculated 'sleep quality index' can be compared to a more elaborate reference which takes into account the female menstrual cycles, as shown at FIG. 6. The reference curve C has a 28-day periodicity since the average 'sleep quality index' depends on the current moment in the female menstrual cycle.

In this second embodiment, the life parameters at particular concern are:
75—average ambient noise level
76—level of air pollutants,
73—alcohol intake in the evening, During a time period DT1', there is more noise and/or more pollutants. As a consequence, at instant T1, the 'sleep quality index 6' of the user is found to be lower than C1. The system thus record a break event at T1, and stores at least the sample values of: noise level 75, level of air pollutants 76, alcohol intake per day 73, over DT1'. This constitutes a break event record in the remnant memory that will be used later.

Later, at time period DT2', similar conditions are collected about noise level 75, level of air pollutants 76, alcohol intake per day 73. Therefore, at T2, a user notification is issued by the system to warn the user, because same causes produce same effects, that the user might experience poor quality sleep if he/she does not change the air in the room and close fully the window.

It is to be noted that the time depth of data collection can be different from one life parameter to another, and also the sampling frequency F1 can be different from one life parameter to another.

It is to be noted that the calculation operations and storage can be done either in the smartphone 3 and/or in the Internet server 4. More generically the calculation operations are performed by a computation device, whatever the task(s) entrusted respectively to the smartphone 3 and/or in the server 4.

Figure 4:
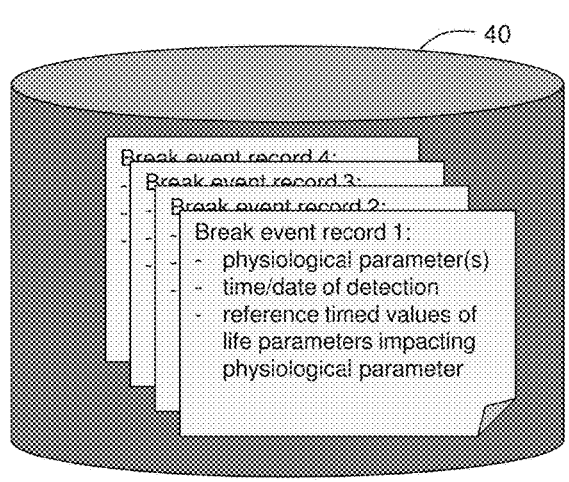
FIG. 4 shows the database in which are stored various break event data.

More particularly, there is provided a database 40 in the server 4 to store the break event records, as shown in FIG. 4. According to a preferred embodiment, most of the calculations are performed in the server 4, the smartphone 3 is used merely as a user interface to provide user notice(s), and also to enable the user to select preferences, presets, and various acknowledgments.

The invention claimed is:
1. A method to monitor movements and at least body temperature or heart rate of an individual and give a notice to said individual about said individual's sleep quality conditions, said method comprising a first set of steps:
   a—collect over a first time period, said movements and at least body temperature or heart rate of the individual with a bed mat sensor, and a plurality of life parameters,
   b—calculate, by means of a computation device, a data of interest from collected samples of the movements and at least body temperature or heart rate, and monitor the evolution over time of said data of interest, the data of interest being a quality sleep index,
   c—detect, by the computation device, an unexpected or inadvertent deviation in the evolution over time of said data of interest, said unexpected or inadvertent deviation forming a break event, occurred at a first instant (T1),
   d—store, in remnant memory of the computation device, the previously collected values of the plurality of life parameters over a first time window DT1 (T0-T1) preceding said break event, to form a reference values collection of life parameters, attached to said individual and to the break event,
said method comprising a later, second set of steps:
   e—collect over a second time period, the same values of said plurality of life parameters,
   f—compare said values of the life parameters collected over the second time period to the reference values collection of life parameters stored in remnant memory by the computation device, and if the difference is less than a predefined threshold, give a notice to the individual by a portable communication device, wherein the bed mat sensor is configured to exchange data with the portable communication device, and the computation device is connected to the portable communication device.

2. The method according to claim 1, wherein the life parameters are chosen among a list comprising:
geolocation of the individual user,
time in day, moment in week, moment in month, season moment in year,
number of messages exchanged over social network(s),
type of current activity (work, holiday, travelling, sports, visiting friends, visiting family),
level of physical activity, number of steps done per day,
average food intake per meal/day/week,
average alcohol intake per meal/day/week,
tobacco smoking per day/week
drug/medicine consumption per day/week
time spent watching TV (or videos on computer)
environmental parameters around the user (temperature, air quality, pollutants, sound/noise levels)
weight, weight variation,
blood pressure, heart rate variability.

3. The method according to claim 1, wherein each of the plurality of the life parameters is sampled/collected and stored momentarily in a rolling window (TR) having a time depth no less than the first time window DT1.

4. The method according to claim 1, wherein at step c—, the detection of an unexpected or inadvertent deviation in the evolution over time of said data of interest is performed with reference to a predefined interval of expected values.

5. The method according to claim 1, wherein at step c—, the detection of an unexpected or inadvertent deviation in the evolution over time of said data of interest is performed using a CUSUM control chart.

6. The method according to claim 1, wherein at step c—, the detection of an unexpected or inadvertent deviation in the evolution over time of said data of interest is performed with reference to a reference curve giving a predefined expected evolution of the data related to the movements and at least body temperature or heart rate as a function of time or at least one life parameter.

7. The method according to claim 1, resulting, upon iteration, in the storing in a database of a plurality of break event records, each record comprising the movements and at least body temperature or heart rate, the time/date of detection of the break event, and the reference values collection of life parameters attached to this break event.

8. A system comprising at least a bed mat sensor and at least a computation device, the system being configured to:
a—collect over a first time period, movements and at least body temperature or heart rate of an individual by the bed mat sensor and a plurality of life parameters,
and, at the computation device:
b—calculate by means of the computation device, a data of interest from collected samples of the physiological parameter, and monitor the evolution over time of said data of interest, the data of interest being a quality sleep index,
c—detect, by the computation device, an unexpected or inadvertent deviation in the evolution over time of said data of interest, said unexpected or inadvertent deviation forming a break event, occurred at a first instant (T1),
d—store, in remnant memory of the computation device, the previously collected values of the plurality of life parameters over a first time window DT1 (T0-T1) preceding said break event, to form a reference values collection of life parameters, attached to said individual,
the system being further configured to later perform, at the computation device:
e—collect over a second time period, the same values of said plurality of life parameters,
f—compare said values of the life parameters collected over the second time period to the reference values collection of life parameters stored in remnant memory by the computation device, and if the difference is less than a predefined threshold, give a notice to the individual by a portable communication device.

9. The system according to claim 8, wherein the data computation device comprises a bedside unit.

10. The system according to claim 9, wherein the bedside unit is able to assess the individual's sleep phases based on the collected movements and at least body temperature or heart rate.

11. The system according to claim 8, wherein the bed mat sensor is configured to exchange data with the portable communication device, and the computation device is connected to the portable communication device.

12. The system according to claim 11, wherein the portable communication device is a smartphone, and the computation device is an internet server.

13. The method according to claim 1, wherein the bed mat sensor is formed as a pneumatic inflatable bladder linked to an electronic unit which transduces pressure information into movements.

14. The method according to claim 1, wherein the movements are ballistographic movements.

* * * * *